United States Patent [19]

Thurman et al.

[11] Patent Number: 5,301,319

[45] Date of Patent: Apr. 5, 1994

[54] DATA STORAGE AUDIT TRAIL

[75] Inventors: Audree Thurman, Phoenix; Stanley Person, Mesa; Richard Shelton, Mesa; Ronald Norden-Paul, Mesa, all of Ariz.

[73] Assignee: Emtek Health Care Systems, Inc., Tempe, Ariz.

[21] Appl. No.: 980,135

[22] Filed: Nov. 23, 1992

Related U.S. Application Data

[63] Continuation of Ser. No. 409,230, Sep. 15, 1989, abandoned.

[51] Int. Cl.⁵ .............................................. G06F 15/40
[52] U.S. Cl. .............................. 395/600; 364/DIG. 2; 364/974; 364/963.3; 364/957.3
[58] Field of Search .......................................... 395/600

[56] References Cited

U.S. PATENT DOCUMENTS

| | | | |
|---|---|---|---|
| 3,940,742 | 2/1976 | Hudspeth et al. | 340/172.5 |
| 4,591,974 | 5/1986 | Dornbush et al. | 364/200 |
| 4,611,298 | 9/1986 | Schuldt | 364/900 |
| 4,646,229 | 2/1987 | Boyle | 364/200 |

Primary Examiner—Gareth D. Shaw
Assistant Examiner—Kakali Chaki
Attorney, Agent, or Firm—Raymond J. Warren; Walter W. Nielsen; Michael D. Bingham

[57] ABSTRACT

The database is provided with an audit trail for the structure types of the object instances. As a component of an object instance of the database is corrected/changed, the corrected/changed component is substituted for the original component and the original component is linked to the corrected/changed component.

2 Claims, 19 Drawing Sheets

OPEN HIERARCHY DIAGRAM
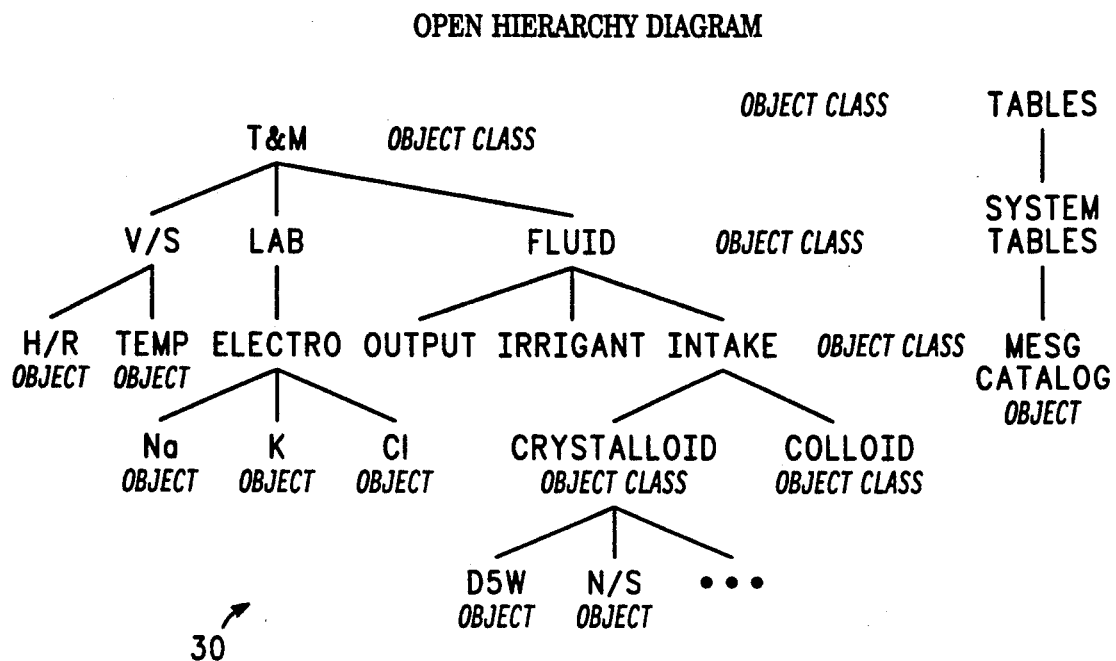
FIG. 2
FIG. 4
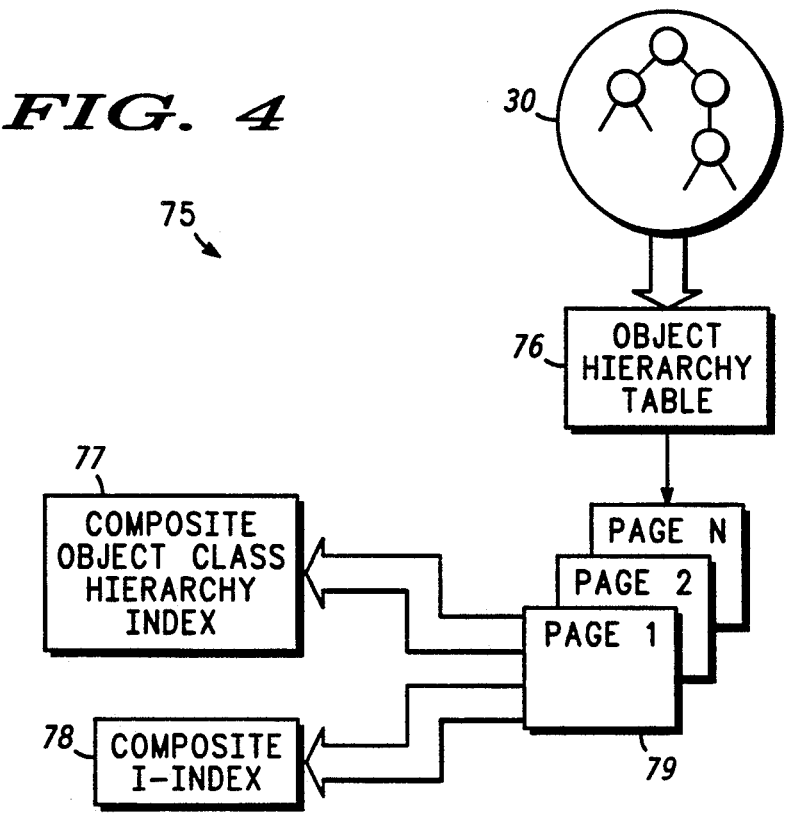

|  |  | 7/7 10:30 | 7/7 11:00 | 7/7 11:30 | 7/7 12:00 | 7/7 12:30 | 7/7 13:00 |
|---|---|---|---|---|---|---|---|
| VITALS | | | | | | | |
| 53A 54A | HEART RATE | 53B  53C | | 53C | 53C | | |
| | BLOOD PRESSURE | 54B | 54C | | 54C | 54C | |
| | TEMP. | | | | | | |
| | RESPIRATION RATE | | | | | | |
| LABS | | | | | | | |
| | CBC HGB | | | | | | |
| | CBC HCT | | | | | | |
| 59B | K+ | | | 59C | | | 59C |
| 60B | Na | 60C | 60C | | | 60C | |
| | BUN | | | | | | |
| | CREAT | | | | | | |

FIG. 3

DATA STORAGE AUDIT TRAIL

This application is a continuation of prior application Ser. No. 07/409,230 filed Sep. 15, 1989, now abandoned.

RELATED INVENTIONS

The present invention is related to the following inventions, all assigned to the assignee of the present invention:

System Control Structure of a Hospital Information System and Method of Using Same, having Ser. No. 116,614, and filed on Nov. 3, 1987;

Clinical Task List with Charting Through the Task List onto Underlying Form and Automatic Updating of Task List, having Ser. No. 572,317 filed on Aug. 24, 1990, continuation of Ser. No. 268,822, and filed on Nov. 7, 1987 (now abandoned);

Clinical Task List with Charting onto Underlying Form and Automatic Updating of Task List, having Ser. No. 572,315 filed on Aug. 24, 1990, a continuation of Ser. No. 268,323, and filed on Nov. 7, 1987 (now abandoned);

Method for Generating Patient-Specific Flowsheets by Adding/Deleting Parameters, having U.S. Pat. No. 4,878,175 issued on Oct. 31, 1989;

Method for Generating a Display, having Ser. No. 540,382 and filed on Jul. 19, 1990, a continuation of Ser. No. 322,740, now abandoned;

A Method for Displaying Information from an Information Based Computer System, having Ser. No. 407,979 and filed on Sep. 15, 1989;

Spreadsheet Cell having Multiple Data Fields, having Ser. No. 408,166 and filed on Sep. 15, 1989;

A Method for Displaying Information from an Information Based Computer System, having Ser. No. 407,836 and filed on Sep. 15, 1989;

Electronic Data Storage Interface, having Ser. No. 408,178 and filed on Sep. 15, 1989;

Method for Updating Data in a Database, having Ser. No. 408,167 and filed on Sep. 15, 1989;

Method for Processing and Storing a Transaction in a Distributed Database System, having Ser. No. 408,164 and filed on Sep. 15, 1989;

Method of Forming a Spreadsheet Display, having Ser. No. 407,972 and filed on Sep. 15, 1989 now abandoned.

FIELD OF THE INVENTION

The present invention relates, in general, to databases and, more particularly, to a data storage audit trail used in a database.

BACKGROUND OF THE INVENTION

The present invention relates to an automated records management system kept in a database form. A database is a collection of logically organized data items. Generally, a database is organized into tables (or pages) which may contain one or more records (or rows). The records are comprised of one or more fields which contain the data.

Such an automatic system has utility, for example, in a hospital based patient record keeping system. Patient record keeping systems are used for maintaining a wide variety of separate, often interrelated, types of medical records concerning patients.

Hand written patient record keeping systems have evolved through many years of careful refinement and enhancement into systems which maintain a detailed manual record of medical information concerning each patient. To meet the needs of different hospital entities (such as doctors, nurses, pharmacy, accounting, laboratory, etc.) a manual record keeping system would require that one piece of information be entered into multiple records.

In a typical manual patient record keeping system a patient chart, usually in the form of a notebook, is maintained at the nursing station for each patient. The notebook is divided into a plurality of individual tabbed sections, such as Physicians Orders, Kardex, Nursing Care Plan, Nursing Assessment, and Laboratory.

Each of the above sections is further subdivided into a number of forms. The forms are those which are appropriate to the individual patient and/or such patient's physician. For example, within the Laboratory section there may appear forms for chemistry, hematology, blood gas, and microbiology.

In addition, a "flowsheet" chart is usually kept at the patient's bedside. On the "flowsheet" chart there are individual areas for medication records, vital signs, intake/output, laboratory results, and other categories which are dependent upon the patient's affliction, such as intravenous (IV) drips.

The flowsheets are often a type of spreadsheet arranged by a progression of time versus a particular parameter. Each of the time/parameter intersections form a cell.

One way of replacing the manual charting system is with electronic databases such as described in the patents and applications referenced in the preceding Related Inventions section. Here a visual display is provided in much the same configuration as present manual charts. Each display provides a time/variable spread sheet consisting of a plurality of data cells.

In this type of electronic database, a cell in a flowsheet may have a form or report associated with it which expands on the information in the cell. This form may be comprised of various attributes and processing rules obtained from one or more object instances of one or more object classes.

An object instance is the instantiation of an object class. An object class is similar to a type (as used in programming languages) in that it defines a structure. The information for these flowsheet cells and the underlying forms, comes from a database containing various patient records. Examples of forms and records are found in copending patent applications "A Method of Forming a Spreadsheet Display" and "Spreadsheet Cell having Multiple Data Fields". During the patient's stay, the information in the database relating to that patient will grow and be physically distributed about the data storage device. Accessing and displaying this information becomes more difficult as the amount of information grows.

Additionally, in a critical care environment, it is a necessity to obtain and display the information in as little time as possible to the health care provider.

An important objective in obtaining a fast turn around time from request to display is the organization and storage of the information in the database, as well as the method used to retrieve the data.

Accordingly, it is an object of the present invention to provide a data storage audit trail in a database which overcomes the above deficiencies and provides the desired advantages.

A further object of the present invention is to provide a data storage audit trail in a database which automatically provides integrated audit trails for object instances and structure types of an object instance.

Another object of the present invention is to provide an electronic data storage interface which physically organizes the stored data in a manner similar to the logical organization of the data, such as the manner in which it will be displayed.

These and other objects and advantages are achieved in accordance with a preferred embodiment of the invention described below.

SUMMARY OF THE INVENTION

A particular embodiment of the present invention consists of a database whose physical organization of data is similar to the logical organization of the data. This physical organization of the data is an indexed matrix organization consisting of object instances having one or more components. Each object instance's components are capable of having their own audit trails. As a component of an object instance of the database has a data cell corrected or changed, the old data cell is maintained and linked to the corrected/changed data cell. This provides an audit trail to the component.

BRIEF DESCRIPTION OF THE DRAWINGS

FIG. 2 shows an object hierarchy diagram utilized by the present invention;

FIG. 3 is a graphical representation of a display generated by a process embodying the present invention;

FIG. 4 shows a block diagram of the process used in retrieval of data from a database;

DETAILED DESCRIPTION OF THE DRAWINGS

Figure 1:
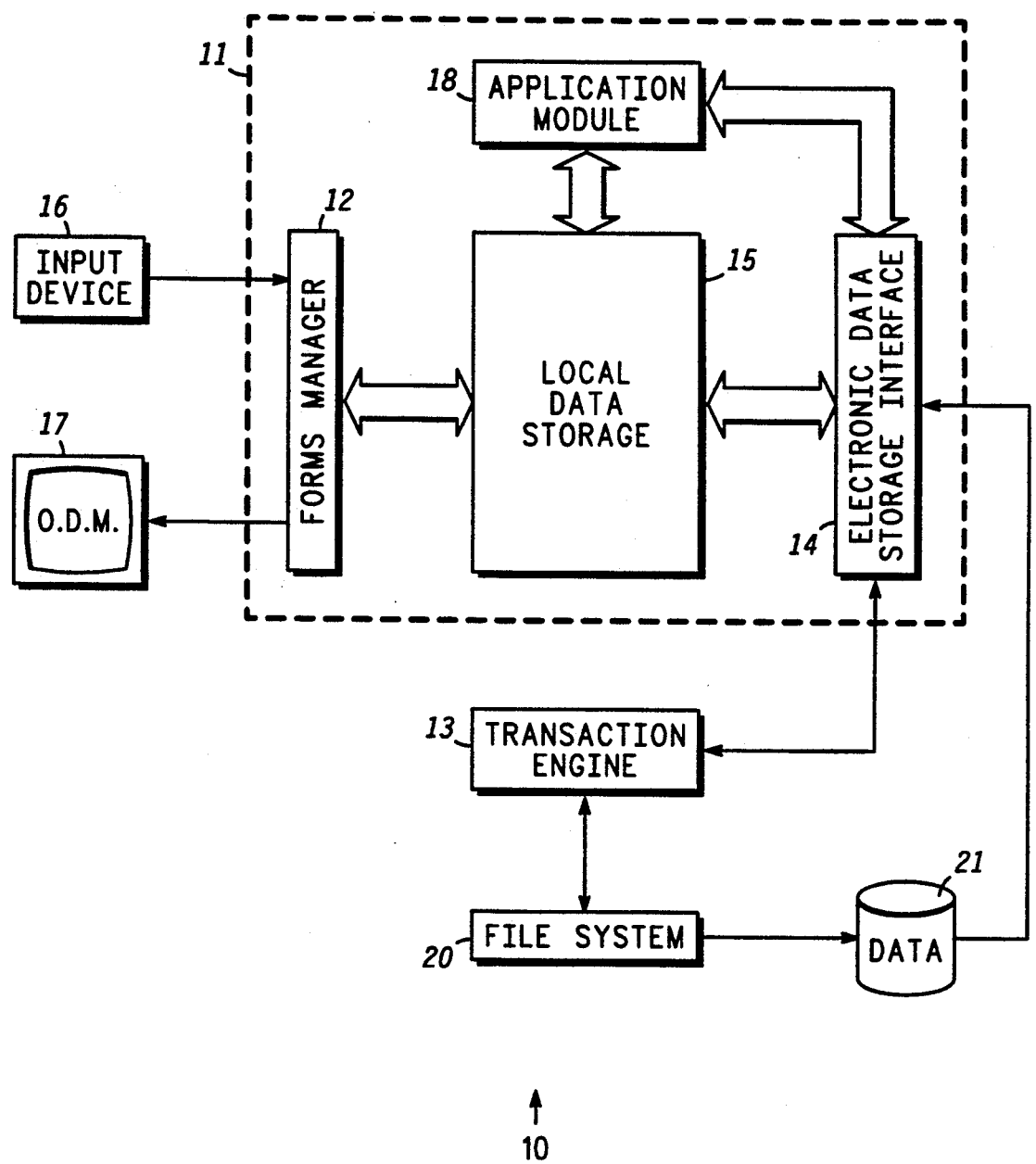
FIG. 1 is a block diagram representing the function of the present invention within a data processing system.

Referring initially to FIG. 1, a block diagram, generally designated 10, representing the function of the present invention within a data processing system is illustrated. A process 11, of which the present invention is a part, is designated by a dashed box. Process 11 consists of a forms manager 12 (described in detail in patent application "Forms Manager"), an electronic data storage interface 14 (embodying the present invention), a local data storage 15, and application modules 18.

These various utilities interact with each other and with elements external to process 11. Some of the external elements consist of a transaction engine 13, an input device 16 (such as a keyboard, touch sensitive screen, light pen, mouse, or the like) and an operator display module 17 (such as a CRT, LCD display, gas plasma display, or the like). It is possible for input device 16 and ODM 17 to be one physical device, such as in the case of a touch sensitive screen.

In addition, a file system 20 is present to manage database 21. Interface 14 interacts with file system 20, through transaction engine 13, to produce the data stored in local data storage 15.

Within database 21 are all object instances of object classes which have been instantiated. An object class is the definition of the structure of object instances of the object class and the hierarchical relationship of the object class with respect to other object classes. An object class is similar to a type (as used in programming languages). An object instance is an instantiation of an object class. An object instance is similar to a data item of a particular type. In this particular embodiment, an object instance consists of a row label and the time-dependent data associated therewith. An object class may have one or more object instances. The collection of object instances is a set of records.

An object class hierarchy is a hierarchical ordering of all object classes. An object hierarchy is illustrated in graphical form in FIG. 2 as a tree 30. The hierarchy of tree 30 is set forth below in table 1. The definition of each object class in the hierarchy can be represented by:

| OH1 | OH2 | OH3 | OH4 | OH5 |.

The entries OH1-OH5 represent levels of object hierarchy that specify a given object class. For example, as shown in Table 1, heart rate is designated by:

| T&M | V/S | H/R | NULL | where:
T&M represents the OH1 class Tasks & Measurements;
V/S represents the OH2 class Vital Signs; and
H/R represents the object Heart Rate.

TABLE I

| T&M | V/S   | H/R      | NULL       |     |
|-----|-------|----------|------------|-----|
| T&M | V/S   | TEMP     | NULL       |     |
| T&M | LAB   | ELECTRO  | Na         |     |
| T&M | LAB   | ELECTRO  | K          |     |
| T&M | LAB   | ELECTRO  | Cl         |     |
| T&M | FLUID | OUTPUT   | ...        |     |
| T&M | FLUID | IRRIGANT | ...        |     |
| T&M | FLUID | INTAKE   | CRYSTALLOID| D5W |
| T&M | FLUID | INTAKE   | CRYSTALLOID| N/S |

| TABLE I-continued | | | | |
|---|---|---|---|---|
| T&M | FLUID | INTAKE | CRYSTALLOID | ... |
| T&M | FLUID | INTAKE | COLLOID | ... |
| TABLES | ... | | | |
| TABLES | SYSTEM TABLES | MESGCAT | NULL | |
| TABLES | SYSTEM TABLES | ... | | |
| OBJECT HIERARCHY (sample) | | | | |

OBJECT HIERARCHY (sample)

In addition to traditional data organization methods (e.g. tables, row-indexed) data can be organized in the form of an indexed matrix. In addition to a row label, indexed matrix object instances have a collection of data cells organized with respect to time. For example, a heart rate object instance would have a row label containing information such as who added the object instance to the database, when it was added, which patient the heart rate belongs to, etc. The heart rate object instance would also have a collection of cells, each containing such information as: a particular heart rate, who recorded the heart rate, when this particular heart rate value was measured, etc. Thus, the indexed matrix data in a database can logically be viewed as a matrix of data cells identified by a row label and a time.

Index matrix object classes are also classified, according to their instantiation over time, as being: ultra sparse, sparse, dense, or ultra dense. An ultra sparse object class is one which is generally instantiated only a few times during a hospital stay. An example of an ultra sparse object class would be the admitting data of a patient, weight, etc. Object classes that are sparse are instantiated approximately once per day. An example of a sparse object class would be a lab result. Object classes classified as dense are generally instantiated once per hour. Examples of dense object classes include temperature, heart rate, blood pressure, etc. Finally, object classes which are instantiated every few minutes are classified as ultra dense. Ultra dense data are often obtained from bedside monitors. It should be noted that classification of an object class according to frequency does not impose limitations on the frequency with which data may be entered. For example, it is permissible for an ultra sparse object class to have data entered for a dense or even ultra dense frequency.

For applications such as automation of a hospital flowsheet, the physical organization of the data (indexed matrix) is similar to the logical view of the data (spread sheet).

For example, during operation, the system user, typically a nurse or physician, conducts a dialog with the system through the use of input device 16. The user provides information to or queries the system by means of the input device and receives information from the system by means of the output device.

A sample output display, generally designated 50, is illustrated in FIG. 3. Form 50 illustrates two groups of tiles, a vitals group 51 and a labs group 52. Vitals group 51 contains four tiles: a heart rate tile 53, a blood pressure tile 54, a temperature tile 55, and a respiration rate tile 56. The labs group consists of: a CBC/HGB (Complete Blood Count/HemoGloBin) tile 57, a CBC/HCT (Complete Blood Count/HematoCriT) tile 58, a K+ (Potassium) tile 59, a Na (Sodium) tile 60, a BUN (Blood Urea Nitrogen) tile 61, and a CREAT (CREATinine) tile 62.

Each of tiles 53–62 comprises several cells. For example, heart rate tile 53 has a group cell 53A and a title cell 53B. In a group, such as group 51, the name of the group may or may not be printed. Generally, only the first tile in the group, here tile 53, will designate the group name. Cell 53B contains the title, here the title is "Heart Rate". The remaining cells of tile 53 are data cells 53C. One cell 53C is provided for every time period listed on the display. Cells 53C are spreadsheet type cells in that they repeat with time whereas cells 53A and 53B are non-spreadsheet cells that do not repeat with time. In tile 54, the group cell 54A is left blank since the group is displayed previously. However, the title cell 54B of tile 54 is labeled Blood Pressure. The data cells 54C of tile 54 are then aligned with the time intervals.

Because the physical organization of the object instance is similar to the format in which they are displayed, the retrieval time of the object instances is significantly reduced. For example, the object hierarchy of Table 1 is similar to the form illustrated in FIG. 3.

Referring now to FIG. 4, an example of the steps taken to provide the data used to form the display of FIG. 3 is illustrated. Upon start-up, the system retrieves the system hierarchy (consisting of all possible object classes), illustrated by tree 30, from database 21. An object class hierarchy table 76, similar to Table 1 is formed from the retrieved object classes.

When particular information is requested, an application will inform the data interface which object instances it desires to receive. Table 76 then accesses pages 79 in the database associated with the desired object instances.

Figure 5:
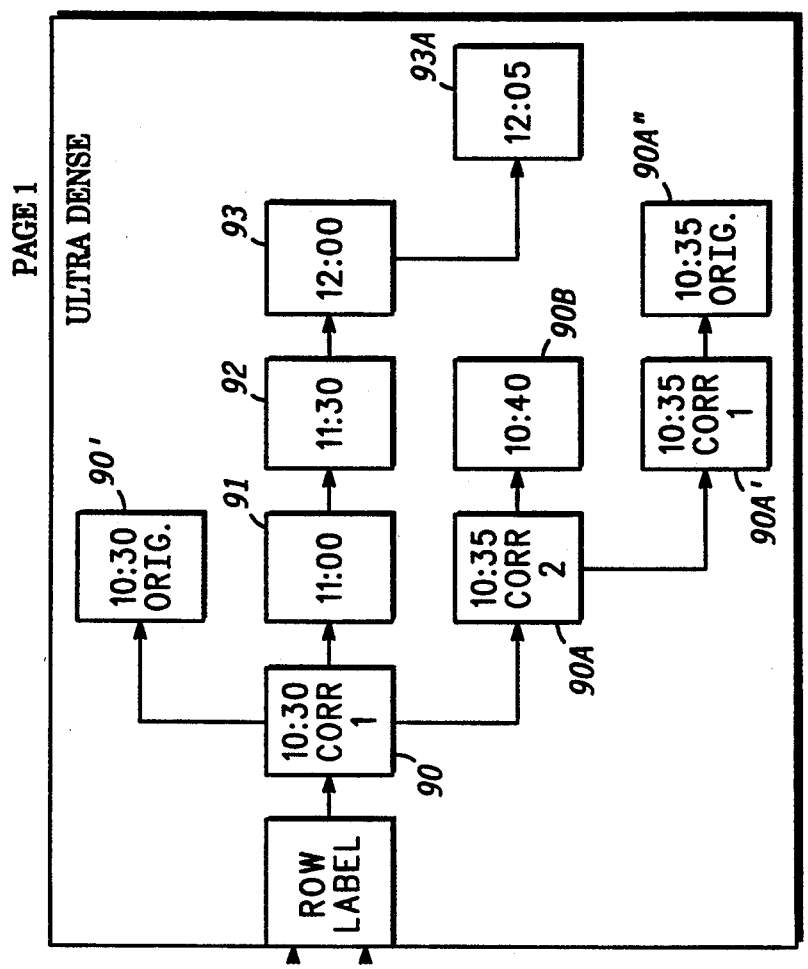
FIG. 5 shows a more detailed block diagram of a page of the database of FIG. 4.

A more detailed block diagram of a page 79 of FIG. 4 is shown in FIG. 5 as page 79'. As described above, object class hierarchy index 77A contains a list of object classes 85 for, in this case, a particular patient. Each page 79' also contains an object class hierarchy index (OCHI) 77A and an I-Index 78A of the objects contained on that page.

At this level of operation, the OCHI functions as a mechanism for accessing object instances of the object classes. At run time, the OCHI object class entries are extended to include an instance number. Object classes may have more than one instance. An I-index is an internal, implementation specific index used to more efficiently access object instances in the data space and items in the OCHI.

On page 79', a heart rate object instance #N 85A is demonstrated. The row label for the heart rate object instance is located at row label address CD. This address is contained in reference column 87 as entry 87A. In addition, there is an I-index column 86 containing a numerical cross-reference to the object class in OCHI 77A. Here, the number 01 is the I-index number 86A which cross-references class 85A.

In this example, an object instance, such as heart rate No. N, consists of a row label and a series of time dependent data cells. A row label is the part of an object instance that contains information that is not time dependent. For object instances without time dependent data the row label will be the entire object instance. A data cell is a collection of attributes in an object instance for a particular time. Therefore, an object instance consists of a row label and zero or more cells.

The layout of Page 1 of database 79' is also illustrated in FIG. 5. Here the row label is linked to a primary cell for a time range. In this example, the primary cell is a 10:30 cell 90. Cell 90 then has a primary link to the next primary cell 91. This then continues through primary cells 92 and 93.

Because readings may be required more frequently than the predefined time period, it may be necessary to provide a secondary link to cells which, chronologically, fall between primary cells. Examples of this are secondary cells 90A and 90B which, chronologically, fall between primary cells 90 and 91. A secondary cell 93A is also shown which follows primary cell 93.

This serves to reduce the access time in that an application searching for cell 93A need only search through four cells, cells 90-93 (one-half hour each) rather than searching through a series of 48 five minute cells.

In addition to the link to secondary cells, there may also be a link to corrected or changed cells such as correction cells 90', 90A', or 90A". These correction cells are generated when, for any reason, an existing cell has data added, removed, or modified.

The corrected data may be handled in one of two ways. The preferred method is to have the new cell inserted at the front of the linked list of cells (before the original cell). This is preferred since, normally, the user will want to view the most recent data available; and, by placing this data in the main search stream, the retrieval time is reduced. Another alternative is to link the newer cells to the original cell and permit the search to extend through the original cell to the changed cells.

Referring again to FIG. 4, after the relevant pages of the database have been determined from the object class hierarchy table 76 in response to a request from an application, the individual object class hierarchy indexes 77A of the pages are combined into a composite object class hierarchy index 77.

Composite index 77 consists of the object classes which would be relevant to that request. All others are omitted. For example, if the hospital patient census were requested, an object class hierarchy index 77 would be generated for all object classes containing data needed for the census. If a particular patient's chart data were requested, an index 77 would be generated for the object classes for that patient's chart (such as a subset of the classes described in Table 1).

Index 77 provides a link from the particular object class name to the database address where the object instance is stored. Composite index 77 indexes an object class name, here an eight byte ASCII string, to a database row address. Because of the size of the object class name, and the corresponding length of time to search through a list of names, a composite I-index 78 is generated from the individual I-indexes 78A of each page. I-index 78 is a high speed numerical index which provides a cross-reference between a two byte index number and the database row address. This serves to reduce the time necessary to retrieve the desired data.

When an application requests indexed matrix data from the database, it will, either by default or specific request, be provided a time dependent range of data. In this situation, the process will begin at a start date/time and work forward until enough timed data has been obtained to fill the display. This process of combining and searching the data pages is referred to herein as binding. An example of this is provided in FIG. 6 where blocks are used to represent pages of data and their relative densities.

Figure 6:
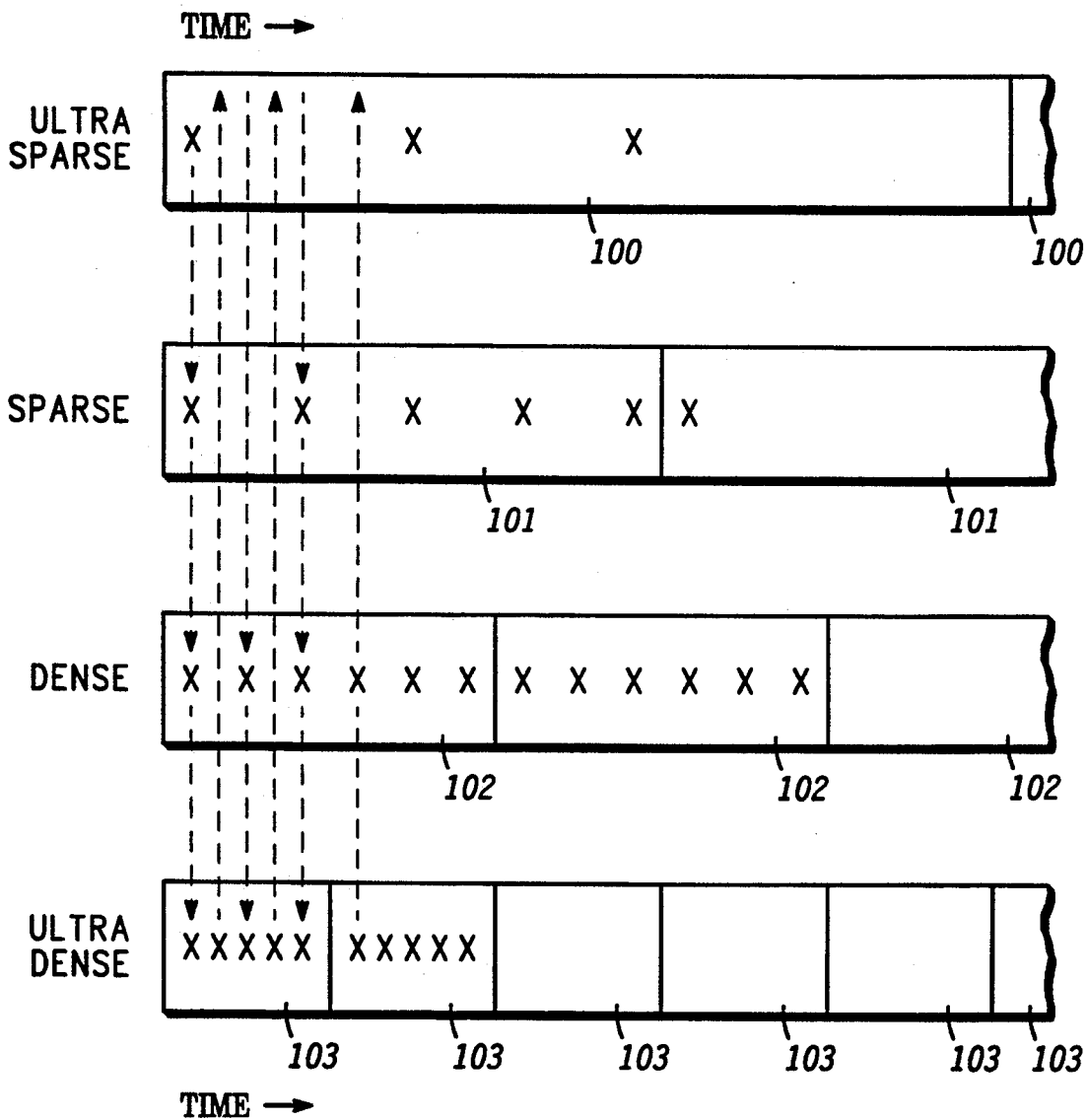
FIG. 6 shows a process by which pages of the database of FIG. 4 are bound and searched to retrieve data.

In FIG. 6, an ultra sparse data page is represented by blocks 100. Sparse data is represented in blocks 101. As shown the sparse data is more compact than the ultra sparse. The dense and ultra dense data blocks, 102 and 103, are each more dense than the previous type of data block. When an application requests data, it may specify a starting time. The process will then search through the various data pages until the available display space is filled.

In the display example of FIG. 3, six time intervals can be displayed at once. The present method would start with the first time period to be displayed and find that data is available in blocks 100-103. The next time period only has data in blocks 102 and 103. This continues until six time periods have been found with data in at least one block. This data is then returned by the process to the application.

It should be noted here that the composite object class hierarchy will not always have all four density types of data. There may only be object classes in the composite object class hierarchy which apply to data pages having sparse and dense data. In that instance, the data retrieval may traverse more time to obtain the number of data cells to be displayed.

Additionally, the user is typically interested in the most recent data. Therefore, the time/data search may commence as of the time of the most recent data entry and proceed back in time until all of the time positions in the display have been filled.

Using the object class |T&M|VS|HR|, the cell and row label definition at define time will be demonstrated. The attributes of a task & measurement (T&M) cell are: the time a parameter (such as heart rate) was entered; whom it was entered by; and the time for which the parameter was entered. These attributes of the class are dictated by the first Object Hierarchy level (T&M). This is illustrated in the listing of Table 2 for the cell structure definition of the task & measurement level of the object class hierarchy.

TABLE 2

```
typedef struct
{
    CHART_TIME entered_at ;
    STAFF_ID entered_by ;
    CHART_TIME time_for ;
}   C_TM;
```

OBJECT HIERARCHICAL LEVEL 1 FOR HEART RATE

The second hierarchical level, Vital Signs (VS), does not add any attributes to this particular cell definition as shown in Table 3

TABLE 3

```
typedef struct
{
    CHART_TIME entered_at ;
    STAFF_ID entered_by ;
    CHART_TIME time_for ;
}   C_VS;
```

OBJECT HIERARCHICAL LEVEL 2 FOR HEART RATE

However, the next hierarchical level, the heart rate (HR), adds a parameter for the heart rate itself to the cell structure definition as shown in Table 4.

TABLE 4

```
typedef struct
{
    CHART_TIME entered_at ;
    STAFF_ID entered_by ;
    CHART_TIME time_for ;
    INT3D hr_value ;
} C_HR;
```

OBJECT HIERARCHICAL LEVEL 3 FOR HEART RATE

The attributes of a task & measurement row label are: the time of the last cell in the object instance (end_row_time); the time the row label was entered; whom the row label was entered by; the time of the first cell in the object instance (start_time_row); an entry flag; a description of a parameter; and a preprint flag. This is illustrated in the listing of Table 5 for the T&M level of the object class hierarchy.

TABLE 5

```
typedef struct
{
    CHART_TIME end_time_row ;
    CHART_TIME entered_at ;
    STAFF_ID entered_by ;
    CHART_TIME start_time_row ;
    char entry_flag[2] ;
    char parameter[26] ;
    char preprint[2] ;
} R_TM;
```

OBJECT HIERARCHICAL LEVEL 1 FOR HEART RATE

The second, and final, hierarchical level (Vital Signs in this example) would add attributes such as a monitor channel, monitor id, site, etc. as shown in Table 6.

TABLE 6

```
typedef struct
{
    CHART_TIME end_time_row ;
    CHART_TIME entered_at ;
    STAFF_ID entered_by ;
    CHART_TIME start_time_row ;
    char entry_flag[2] ;
    char parameter[26] ;
    char preprint[2] ;
    char monitor_channel[9] ;
    int monitor_id ;
    char site[21] ;
    char units[11] ;
} R_VS;
```

OBJECT HIERARCHICAL LEVEL 2 FOR HEART RATE

Figure 7:
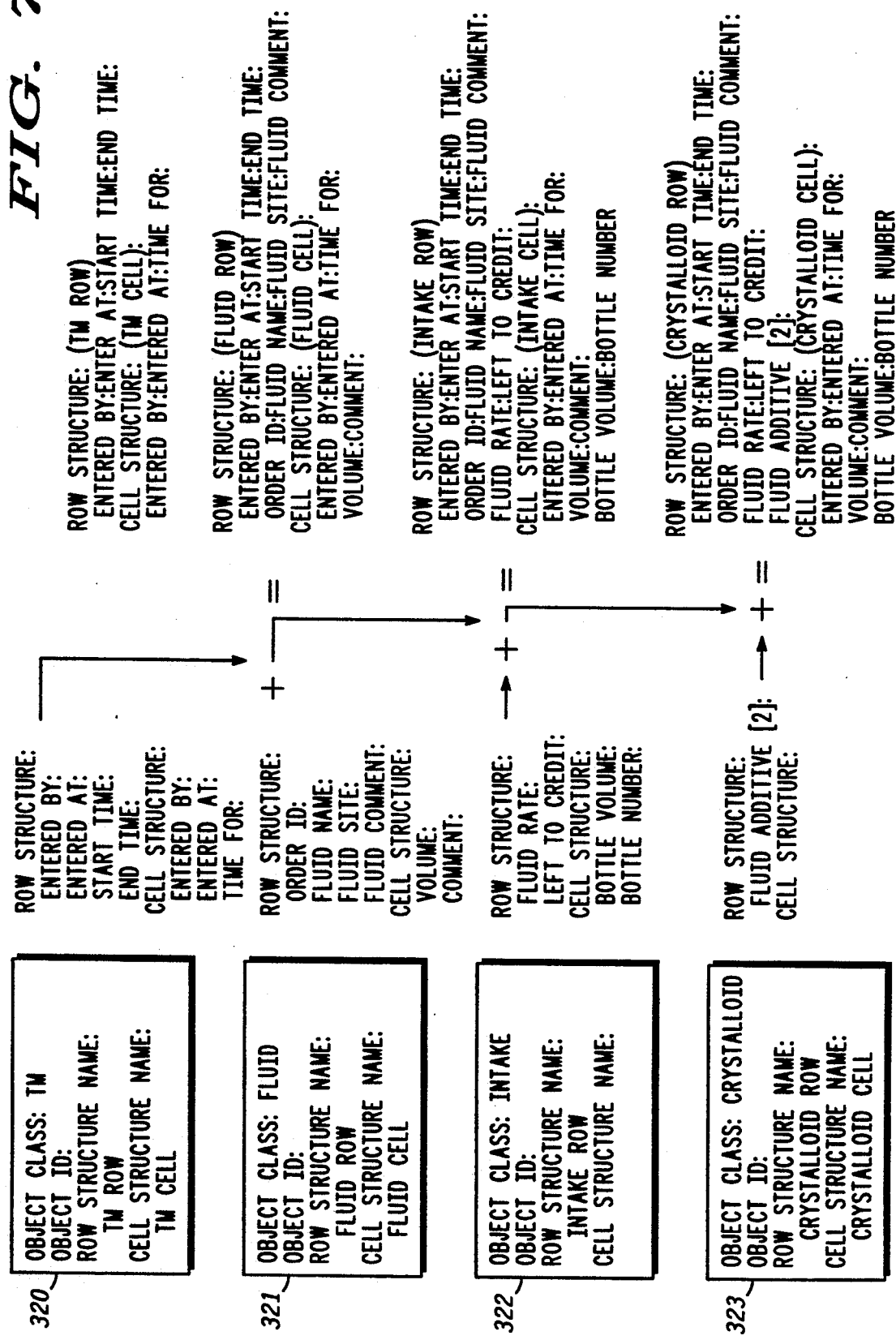
FIG. 7 shows a graphical representation of the hierarchical modifications to an object instance.

This is also illustrated graphically in FIG. 7 where an object class for a Crystalloid intake fluid is shown. The Task & Measurement level (TM) provides row information for: Entered By, Entered At, Start Time, and End Time. This level also provides cell structure information such as: Entered By, Entered At, and Time For.

The next level is the Fluid level. At the fluid level, the row information is enhanced by adding: the Order ID, the Fluid Name, Fluid Site, and Fluid Comment. The cell structure is modified by adding Volume and Comment parameters.

The third level adds Fluid Rate and Left to Credit to the row structure. The cell structure is modified by adding Bottle Volume and Bottle Number.

Finally, the object class is completed by adding the Fluid Additive to the row structure. This provides the final row and cell description for this particular class.

Flow charts describing the process of the present invention are illustrated in FIGS. 8-13B. Pseudo code listings for these flow charts are provided in Appendices A-E. As used in the flow chart descriptions, "row" refers to an object instance and "column" refers to a time across all object instances. The intersection of a row and a column is a particular data cell of an object instance. Starting with FIG. 8, a general flow chart 400 is illustrated. The process commences with the receipt of a data request at a step 401. The process then moves to a subprocess 402 where a set of object classes are defined. Subprocess 402 is described in more detail in FIG. 9.

Once the object classes are defined, a time period is defined over which the data is desired and the various rows containing the object classes are bound, subprocess 403. Subprocess 403 is defined in more detail in FIGS. 10A-10D.

After the rows are bound, the data for the specific object instances are retrieved, step 404. The application then processes, displays, etc. the data, step 405. Once the application has completed its functions, the rows are unbound, step 406, and the process returns, step 407.

Figure 9:
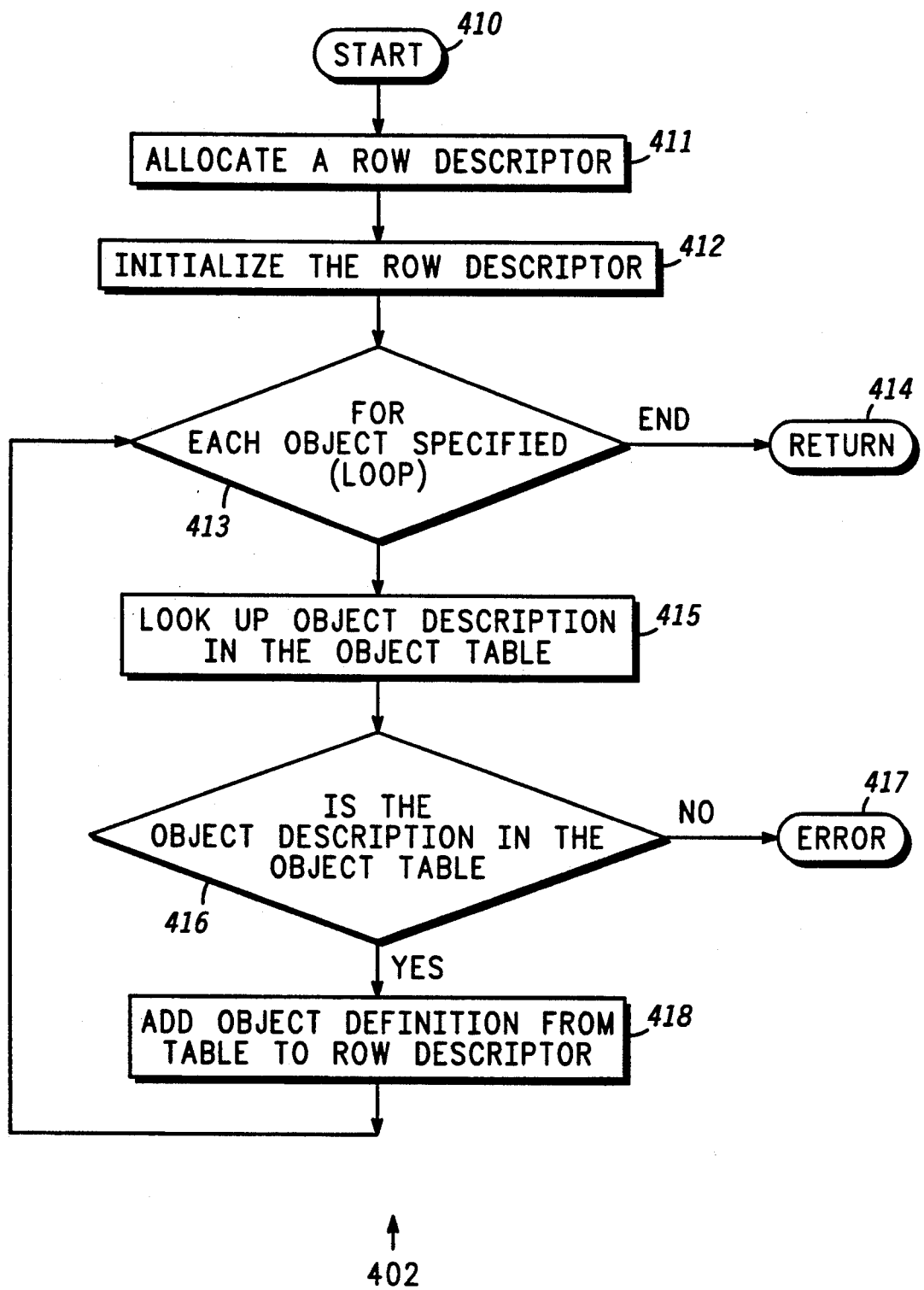
FIG. 9 is a more detailed flow chart of the step of defining an object set in FIG. 8.

Subprocess 402, defining the set of object classes, is illustrated in more detail in FIG. 9, whose pseudo code listing is in Appendix A. Subprocess 402 starts at step 410 and proceeds to step 411 where a row descriptor is allocated. Then in step 412, the row descriptor is initialized.

A row descriptor is used by the application to identify its current view of the database. The row descriptor as used in the present invention is analogous to an operating system file descriptor. Row descriptors are used to access information without needing to know the details of storage format and location of the data sought.

The process then moves to decision step 413, which commences a loop for each object class specified. If there are no more object classes specified, the loop ends and the subprocess returns, step 414.

For each object specified, the process moves to step 415 where the object description is looked up in the object table. If the object class is not listed in the object table, an error has occurred, step 417. If the object class is listed in the table, the object class definition is added to the row descriptors, step 418.

Subprocess 402 then loops back to decision step 413.

Referring now to FIGS. 10A-10D, a more detailed description of subprocess 403 is provided. Pseudo code for this process is contained in Appendix B. The subprocess starts at step 425 and moves to decision step 426 where it determines if object classes are defined for the row descriptors. If the object classes are not defined, an error is generated, step 427.

If object classes are defined, subprocess 403 moves to decision step 428 to determine if there is an indexed matrix object class. If there is no indexed matrix data, subprocess 403 returns, step 429. Indexed matrix data is data with time dependent data cells.

If there is an indexed matrix object class, the row descriptor bind times are set, step 430. Subprocess 403 then moves to decision step 431 to determine if the number of columns is specified. If the number of columns are not specified, subprocess 403 moves to decision step 432, FIG. 10B. In decision step 432, the subprocess determines if both end points are defined. If both are not defined, an error is generated, step 433.

If both end points are defined, subprocess 403 moves to decision step 434 to determine if the direction, between start and end times, is "older". If the direction is older, the subprocess moves to step 435 where the start and end times are switched.

Following step 435, or if the direction is not "older" from step 434, subprocess 403 moves to subprocess 436 where the row list is built. Following this, subprocess 403 returns, step 437.

Figure 10A:
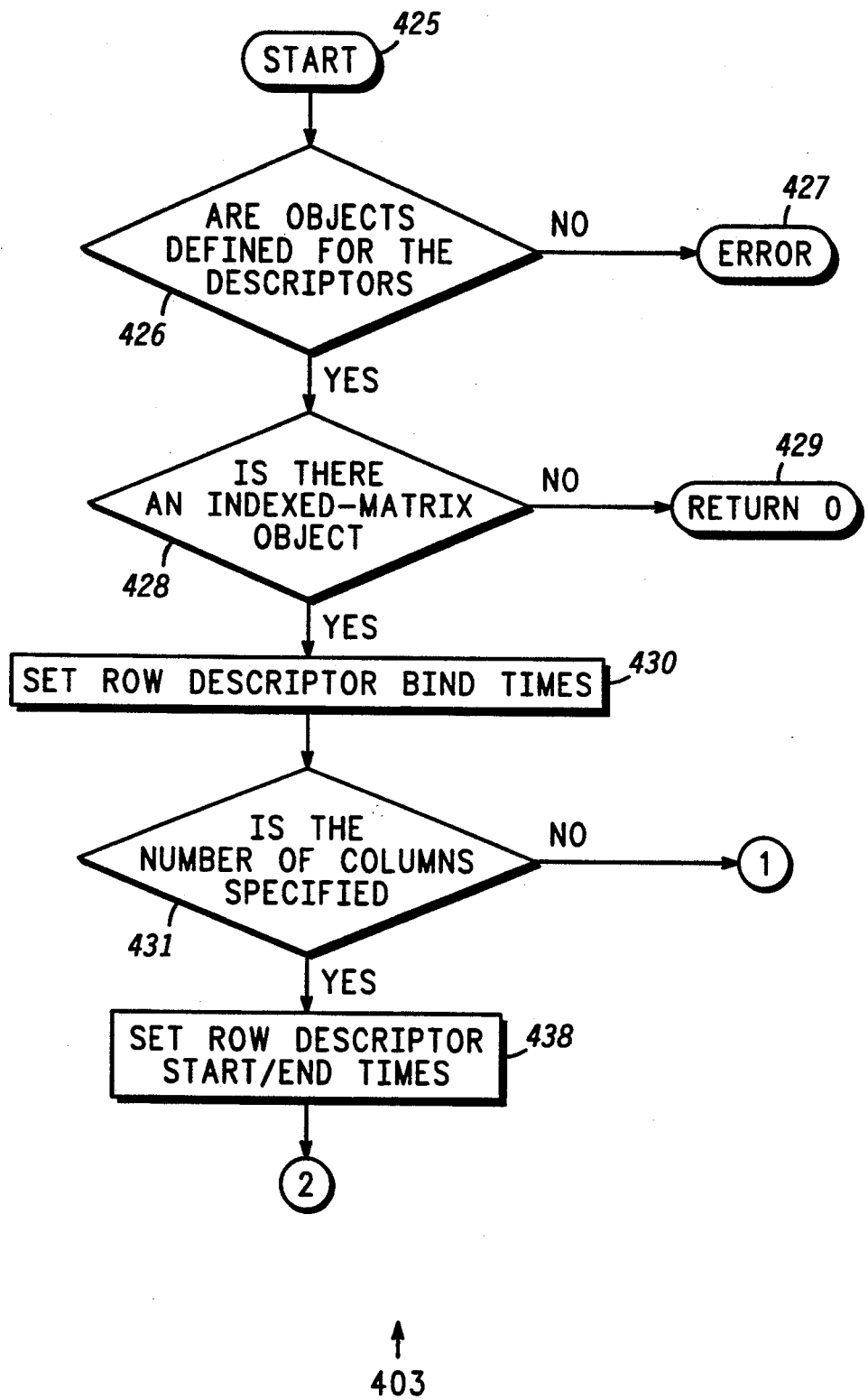
FIGS. 10A-10D illustrate a flow chart for the object binding operation from FIG. 8.
Figure 10B:
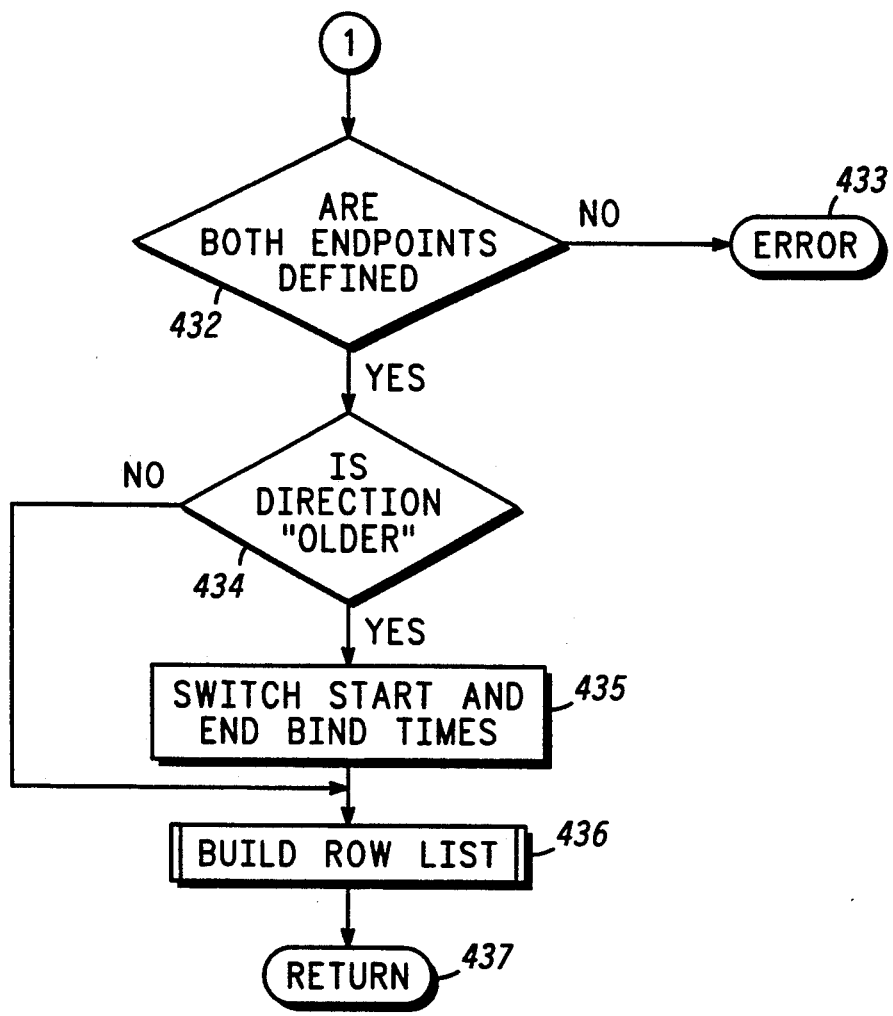
Figure 10C:
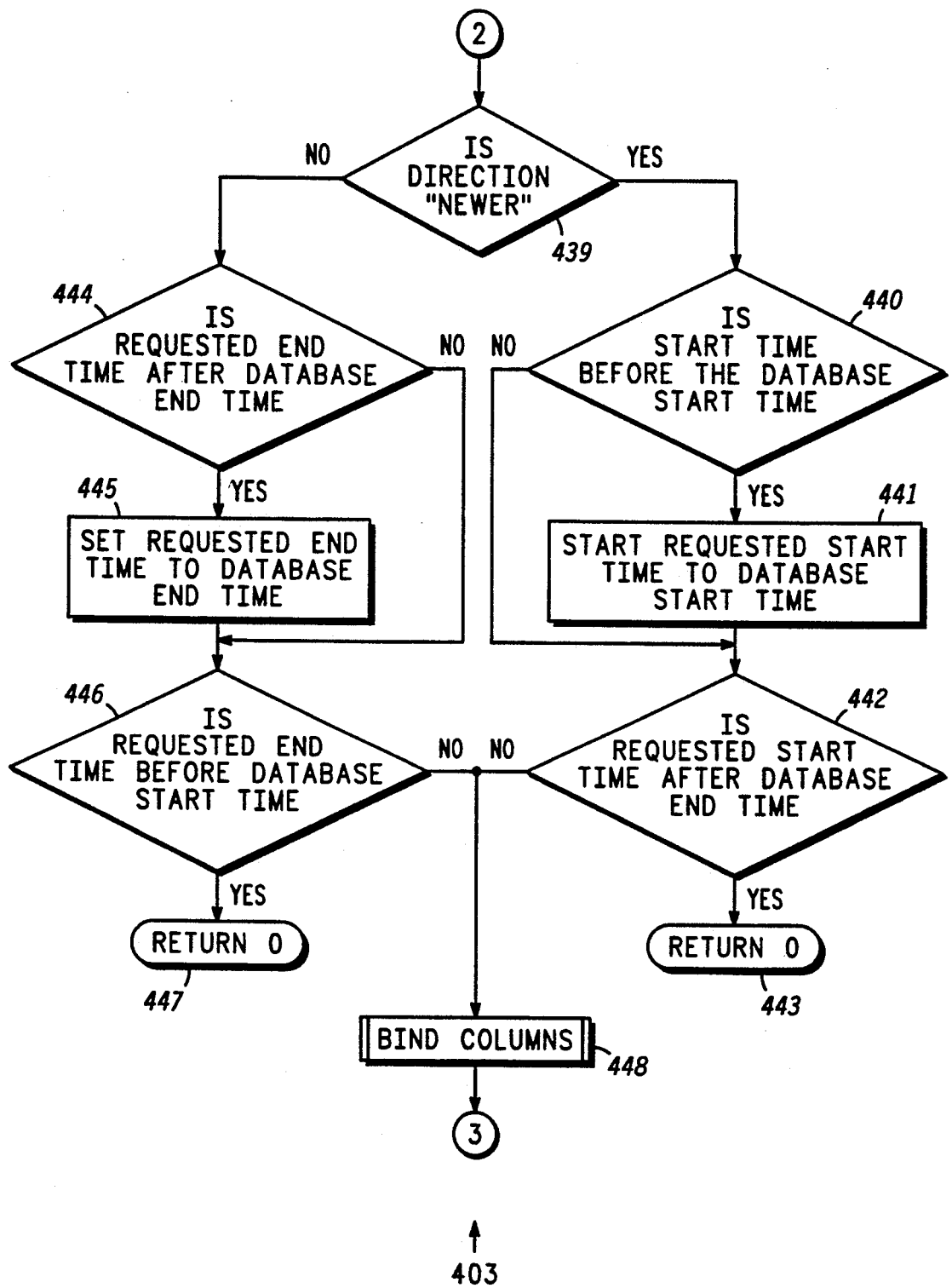

Returning now to decision step 431 of FIG. 10A, if the number of columns is specified, subprocess 403 moves to step 438 where the start/end times for the row descriptors are set. Next, in decision step 439, FIG. 10C, a determination is made as to whether the direction, between start and stop times, is "newer". If the direction is newer, the subprocess moves to decision step 440.

In decision step 440, subprocess 403 determines if the requested start time is before the start time of the database. If the requested start time is earlier, subprocess 403 moves to step 441 where the requested start time is set to the database start time.

Following step 441, or if the requested start time is not before the database start time, the subprocess moves to decision step 442. In decision step 442, the subprocess determines if the requested start time is after the database end time. If the requested start time is after the database end time, subprocess 403 returns, step 443.

If the requested start time is not after the database end time, subprocess 403 moves to subprocess 448 where the columns are bound. Subprocess 448 is illustrated in more detail in FIGS. 12A-12C.

Returning now to decision step 439, if the direction is not "newer", subprocess 403 moves to decision step 444. In decision step 444, the subprocess determines if the requested end time is after the database end time. If the requested end time is after the database end time, the subprocess moves to step 445 where the requested end time is set to the database end time.

If the requested end time is not after the database end time, or following step 445, the subprocess moves to decision step 446. In decisions step 446, subprocess 403 determines if the requested end time is before the database start time. If the requested end time is before the database start time, subprocess 403 returns, step 447.

If the requested end time is not before the database start time, subprocess 403 moves to subprocess 448 where the columns are bound.

Figure 10D:
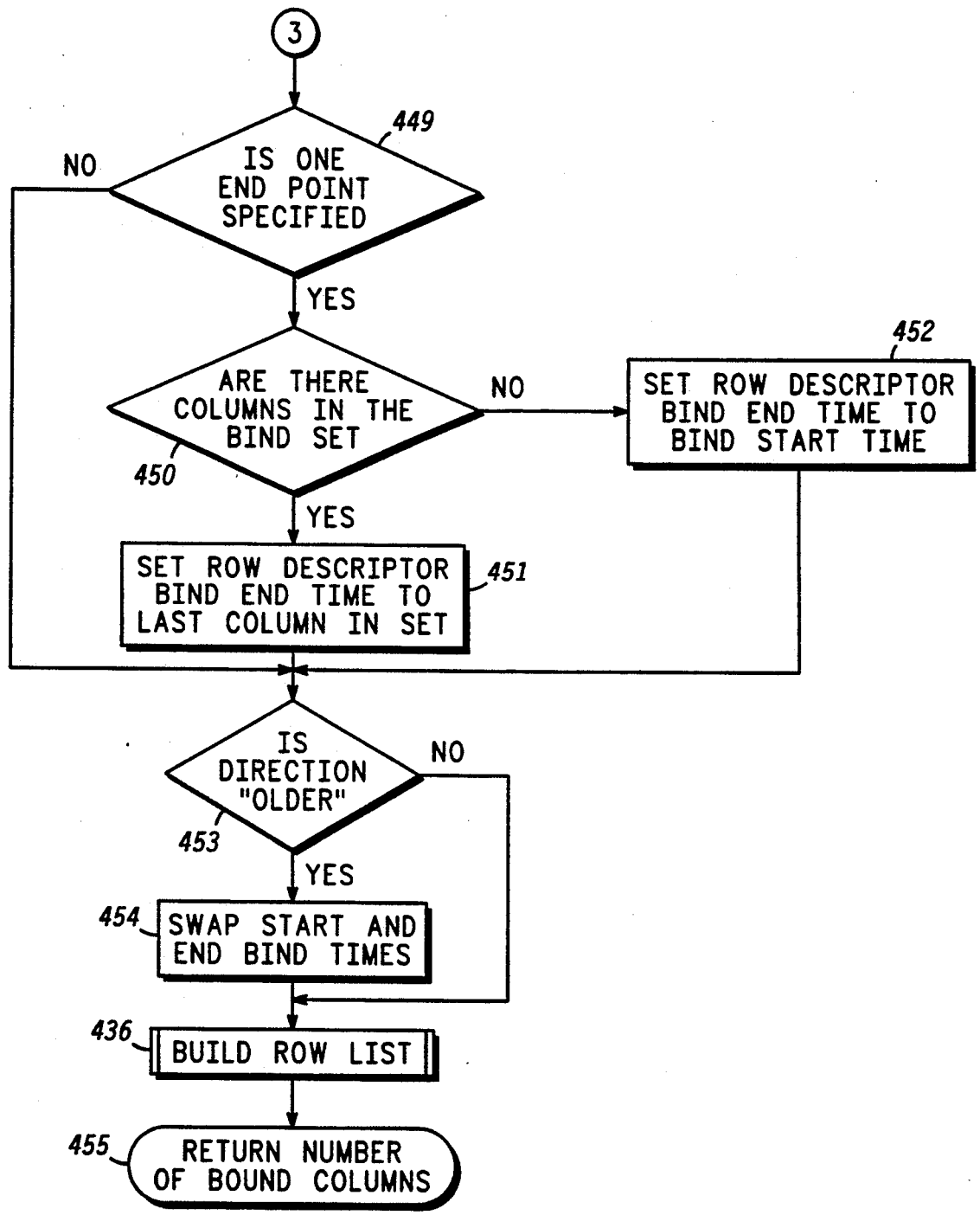

Following the column binding of subprocess 448, subprocess 403 moves to decision step 449, FIG. 10D. In decision step 449, the subprocess determines if only one end point is specified. If only one end point is specified, the subprocess moves to decision step 450 to determine if there are columns in the bind set.

If there are columns in the bind set, the subprocess sets the row descriptor bind end time to the last column in the set, step 451. If there are no columns in the bind set, the subprocess sets the row descriptor bind end time to the bind start time, step 452.

Following the setting of the row descriptor bind end time, steps 451 or 452, or if there is not an end point specified, step 449, subprocess 403 moves to decision step 453.

In decision step 453, the subprocess determines if the direction is older. If the direction is "older", subprocess 403 moves to step 454 where the start and end bind times are switched. Following step 454, or if the direction is not "older", step 453, the subprocess continues to subprocess 436 where the row list is built.

Subprocess 403 then returns, step 455, and provides the number of bound columns.

Figure 11A:
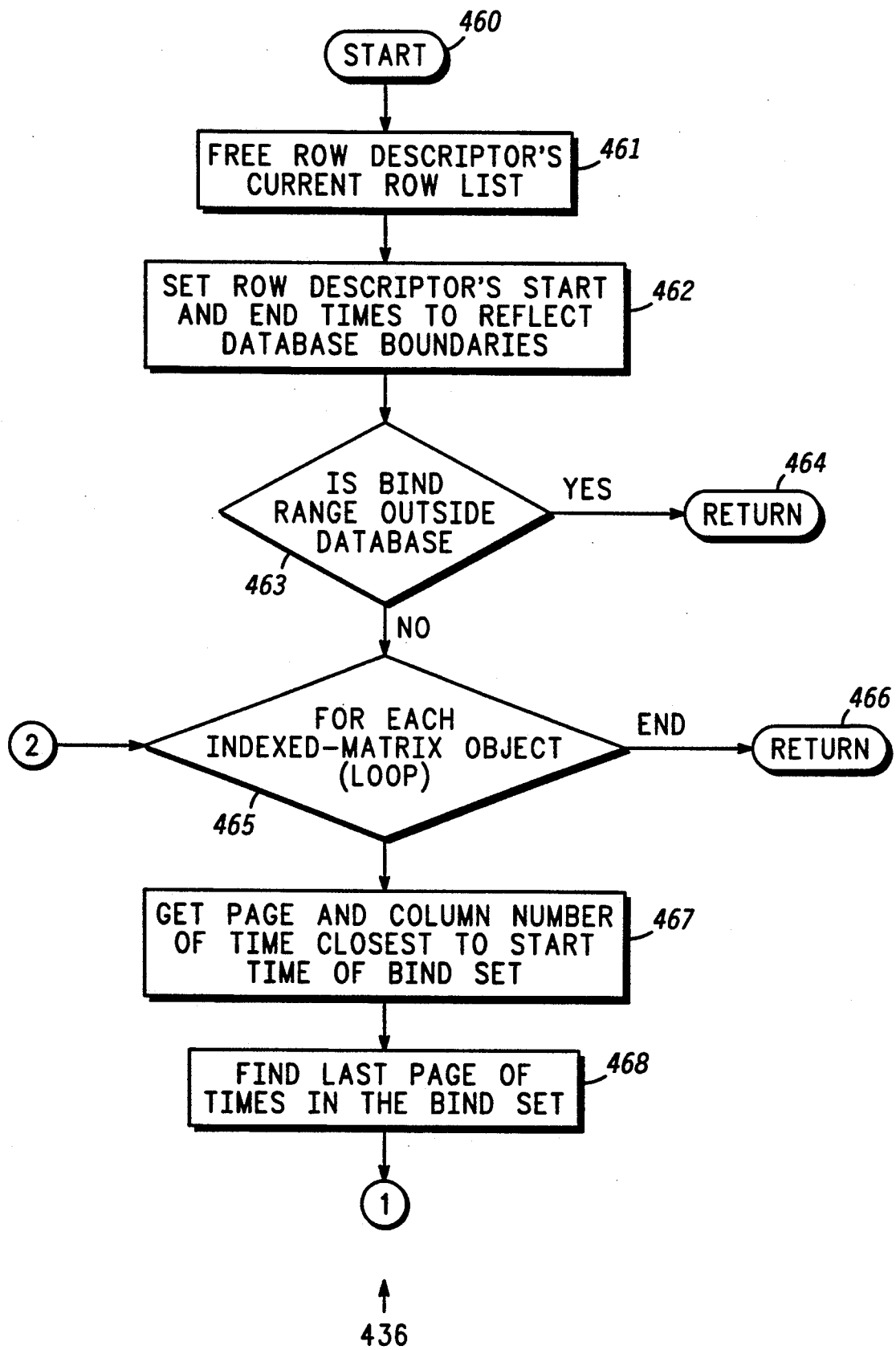
FIGS. 11A and 11B illustrate a flow chart for the building a row list operation of FIGS. 10A-10D.
Figure 11B:
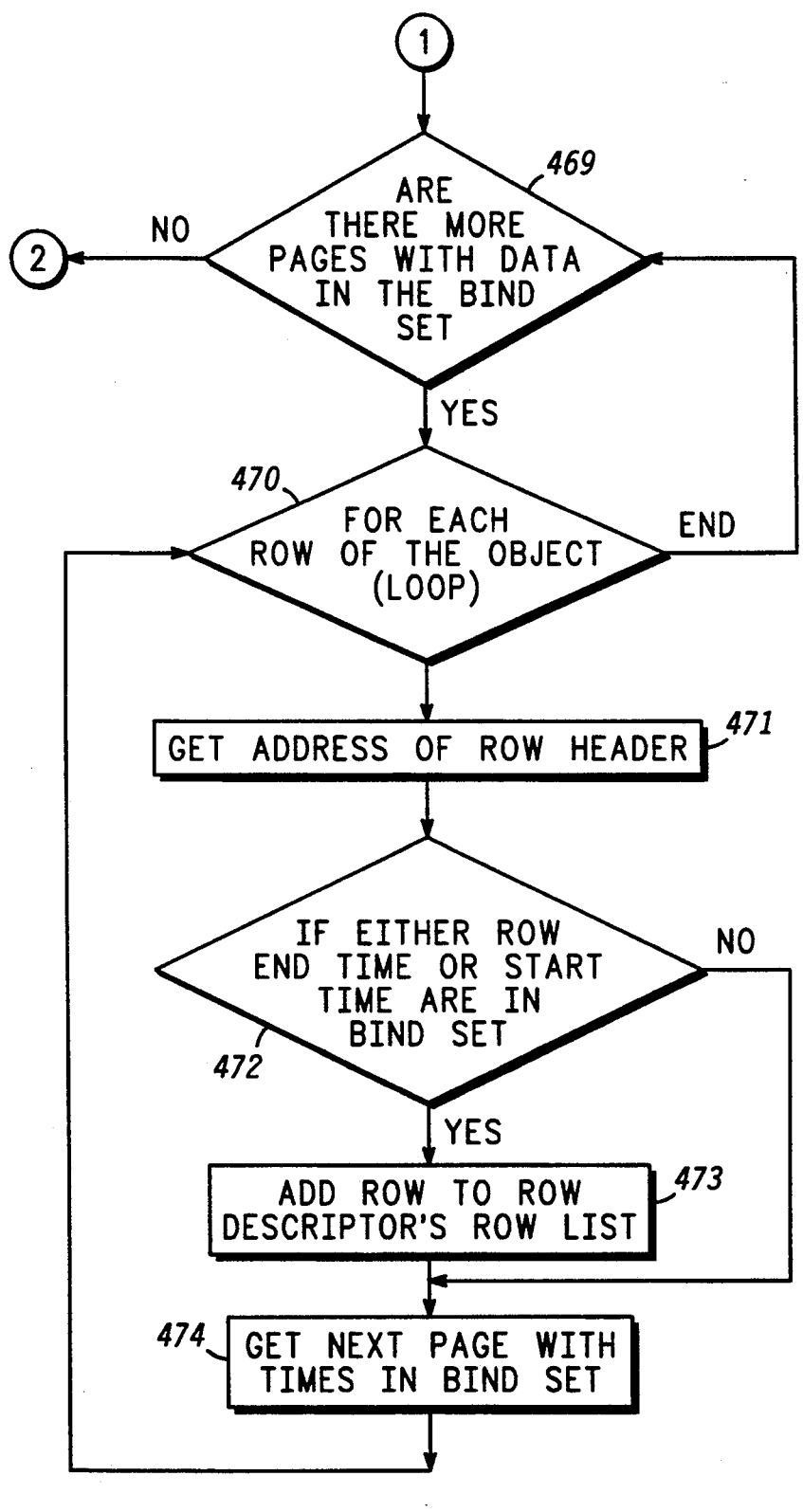

Referring now to FIGS. 11A and 11B, a more detailed description of the build row list, subprocess 436, is illustrated. Pseudo code for subprocess 436 is provided in Appendix C. Subprocess 436 starts at step 460 and moves to step 461 where the current row list of the row descriptor is freed. Next, the row descriptor's start and end times are set to the database boundaries.

Moving to decision step 463, the subprocess determines if the bind range is outside the database. If the bind range is outside the database, the subprocess returns, step 464. If the bind range is not outside the database, subprocess 436 moves to decision step 465.

In decisions step 465, the subprocess starts a loop for each indexed matrix object instance. At the end of the loop, the subprocess returns, step 466. The subprocess then moves to step 467 where it gets the page and column number of the time closest to the start time of the bind set. Next, in step 468, the subprocess finds the last page of the times in the bind set.

Following step 468, the subprocess moves to decision step 469, FIG. 11B, to determine if there are more pages with data in the bind set. If there are no more pages, the process loops back to step 465. If there are more pages, the process moves to decision step 470 to commences another loop for each row of the object class.

If the loop of step 470 has ended, the subprocess moves to step 469. If the loop of step 470 has not ended, the subprocess moves to step 471 and gets the address of the row header. Following step 471, subprocess 436 moves to decisions step 472 to determine if either the row end time or the row start time are in the bind set.

If the row end time or start time are in the bind set, the process moves to step 473 and adds a row to the row descriptor's row list. Following step 473, or if neither the row end time nor row start time are in the bind set, subprocess 436 moves to step 474. In step 474, the subprocess gets the next page with times in the bind set. Subprocess 436 then loops back to step 470.

Figure 12A:
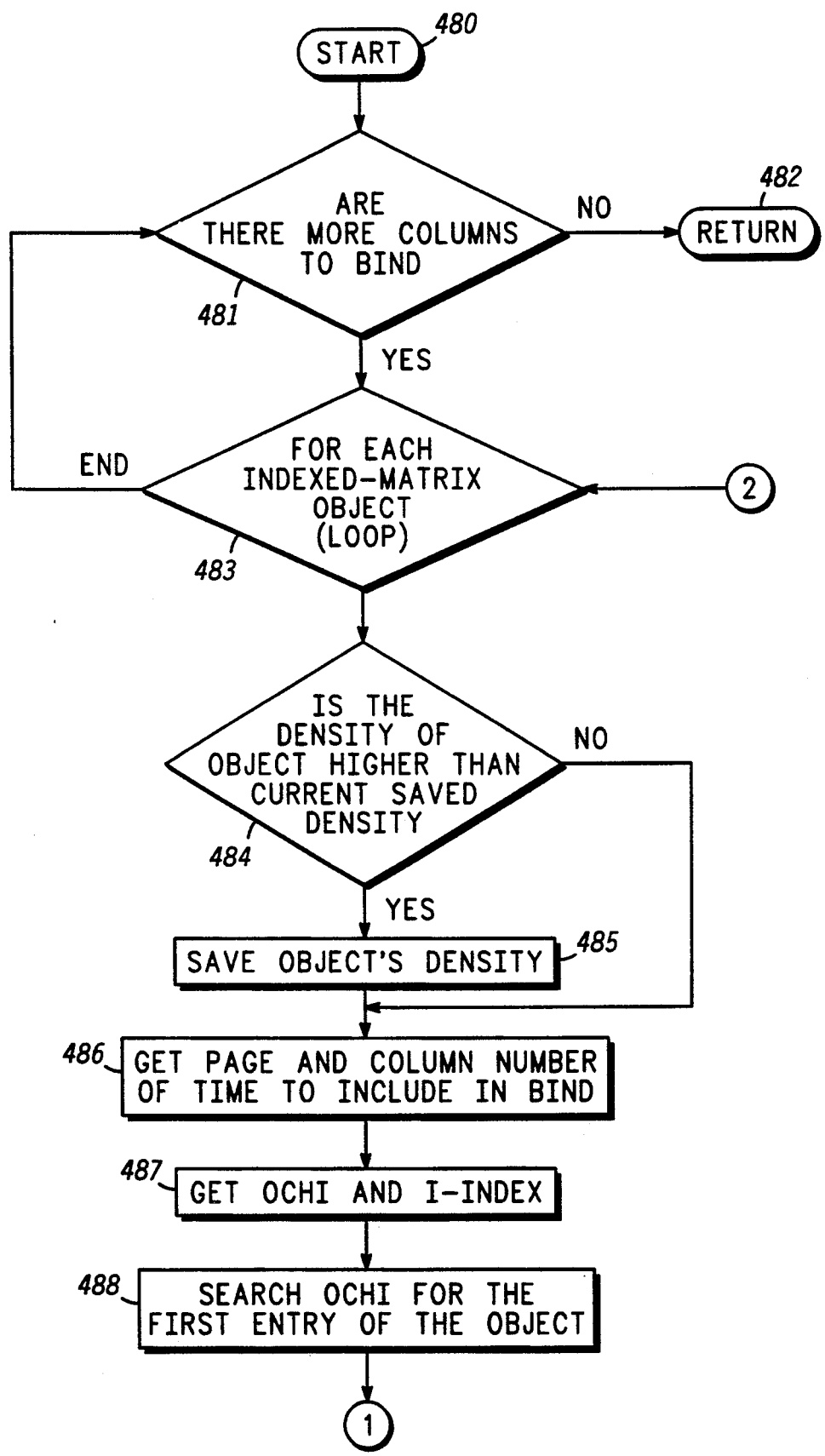
FIGS. 12A-12C illustrate a flow chart for the bind columns operation of FIGS. 10A-10D.
Figure 12B:
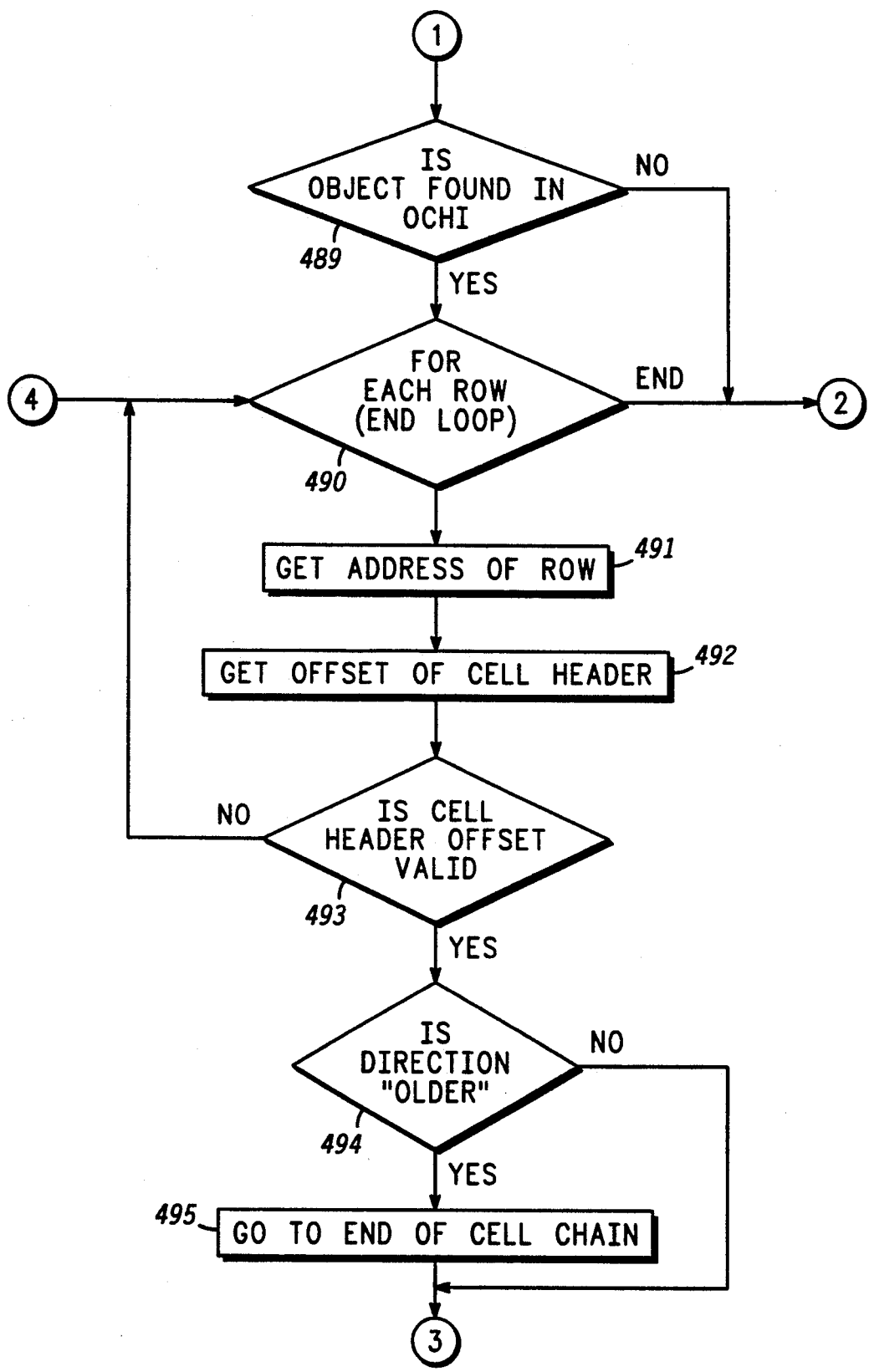
Figure 12C:
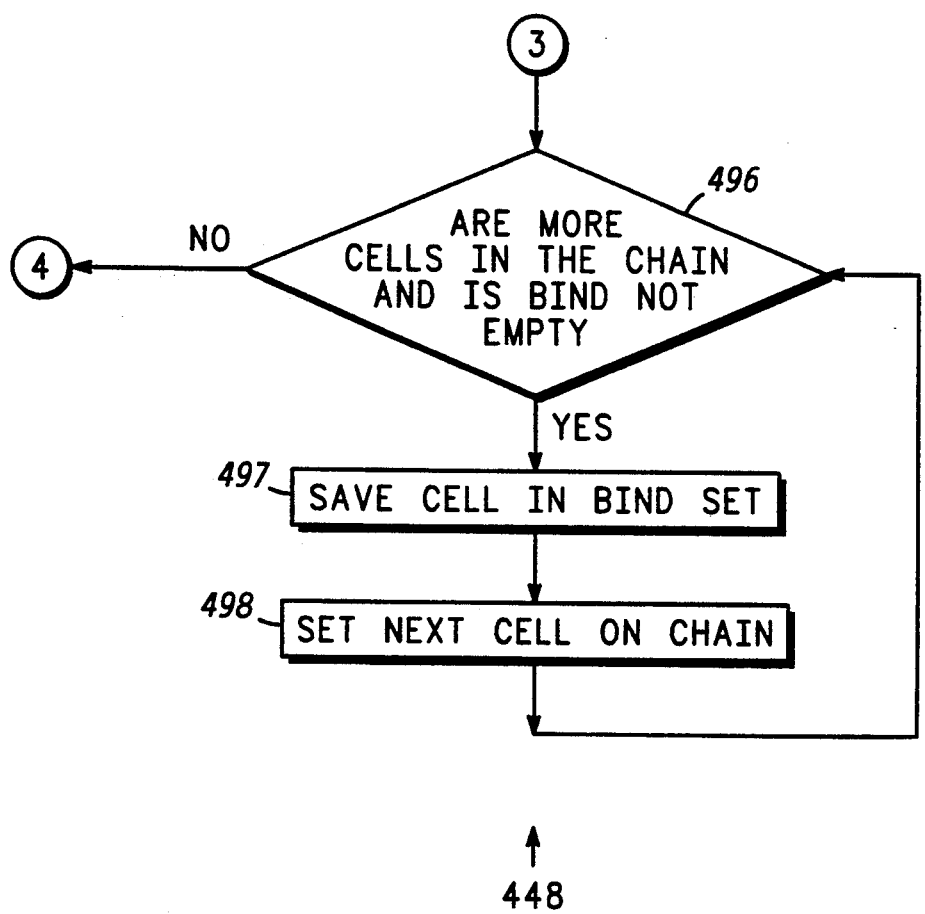

Referring now to FIGS. 12A-12C, bind columns subprocess 448 is illustrated in more detail. Pseudo code for this subprocess is provided in Appendix D. Subprocess 448 starts at step 480 and moves to decision step 481. In decision step 481, the subprocess determines if there are more columns to bind. If there are no more columns to bind, the subprocess returns, step 482.

If there are more columns to bind, the subprocess moves to decision step 483 to start a loop for each indexed-matrix object. If the loop has ended, the subprocess moves to step 481. If the loop has not ended, the subprocess moves to decision step 484 to determine if the density of the object class is higher than the current saved density.

If the density of the object class is higher, subprocess 448 moves to step 485 and saves the object density. Following step 485, or if the object class density is not higher, subprocess 448 moves to step 486 to get the page and column number of the time to include in the bind.

Next, the subprocess gets the OCHI and I-indexes, step 487, and searches the OCHI for the first entry of the object class, step 488. Subprocess 448 then moves to decision step 489, FIG. 12B, to determine if the object class is found in the OCHI. If the object class is not found in the OCHI, the subprocess moves back to step 483.

If the object class is found in the OCHI, the process moves to decision step 490 to start a loop for each row. If the loop has ended, the process moves to step 483. If the loop has not ended, the process moves to step 491 and gets the address of the row. Next, the subprocess gets the offset (or address) of the cell header, step 492.

Following step 492, the process moves to decision step 493 to determine if the cell header offset is valid. If the offset is not valid, the subprocess moves to step 490. If the offset is valid, the subprocess moves to decision step 494.

In decision step 494, the subprocess determines if the direction is "older". If the direction is older, the subprocess goes to the end cell of the chain, step 495. Following step 495, or if the direction is not older, step 494, the subprocess advances to decision step 496, FIG. 12C.

In decision step 496, the subprocess determines if there are more cells in the chain and whether the bind is not empty. If these conditions are not met, the subprocess moves to step 490. If the conditions are met, the subprocess saves the cell in the bind set, step 497, and sets the next cell on the chain, step 498. The subprocess then moves back to step 496.

Figure 8:
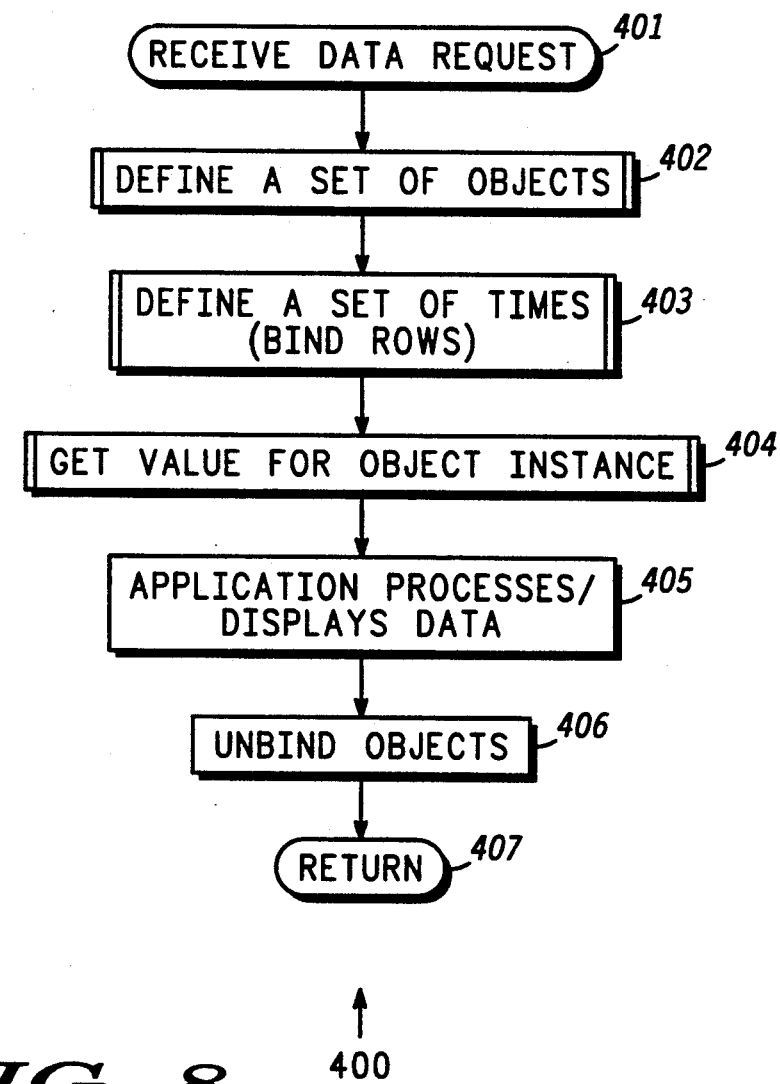
FIG. 8 is a general flow chart of a process embodying the present invention.
Figure 13A:
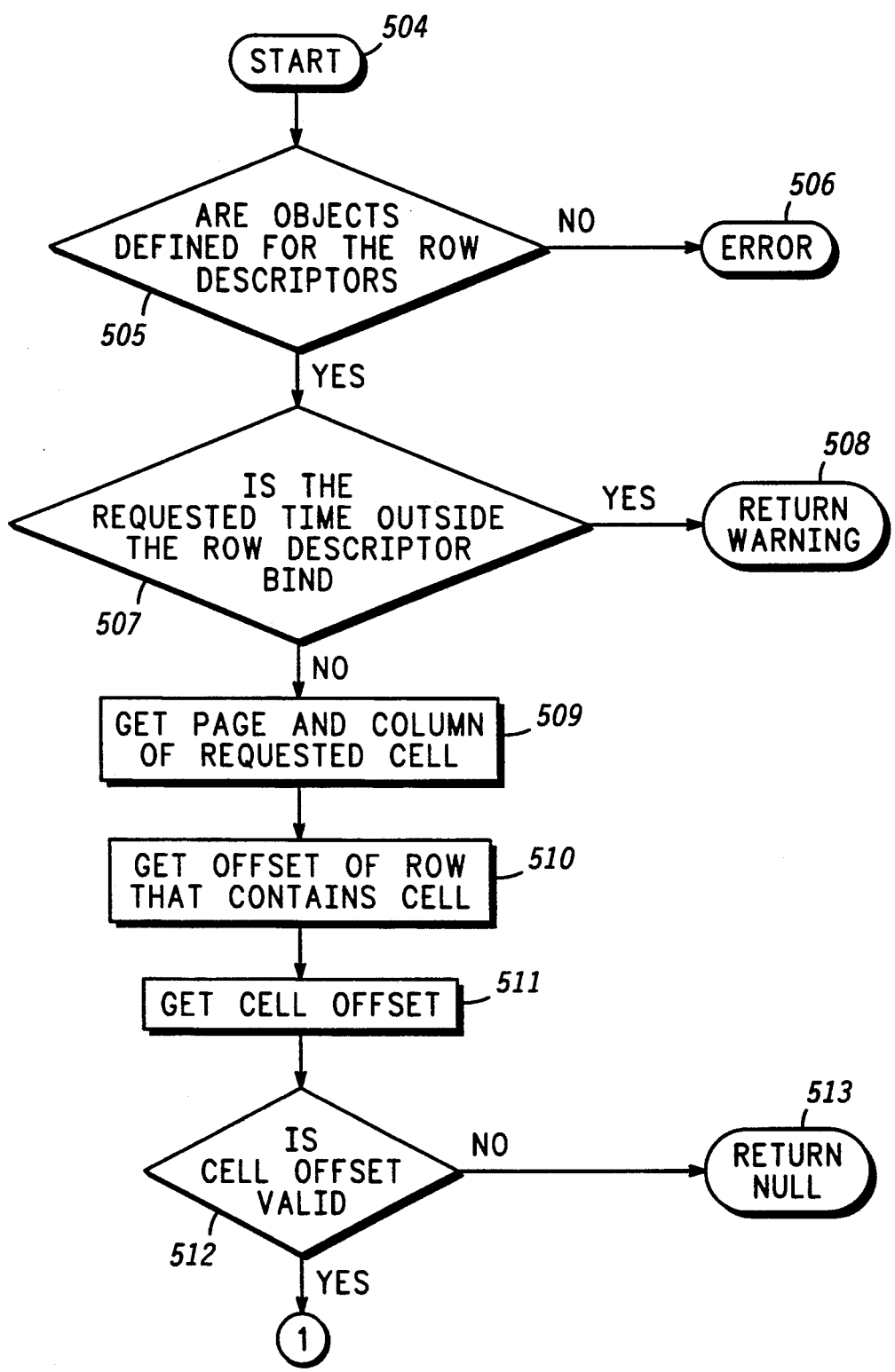
FIGS. 13A and 13B illustrate a flow chart for the operation of getting the value for an object instance of FIG. 8.
Figure 13B:
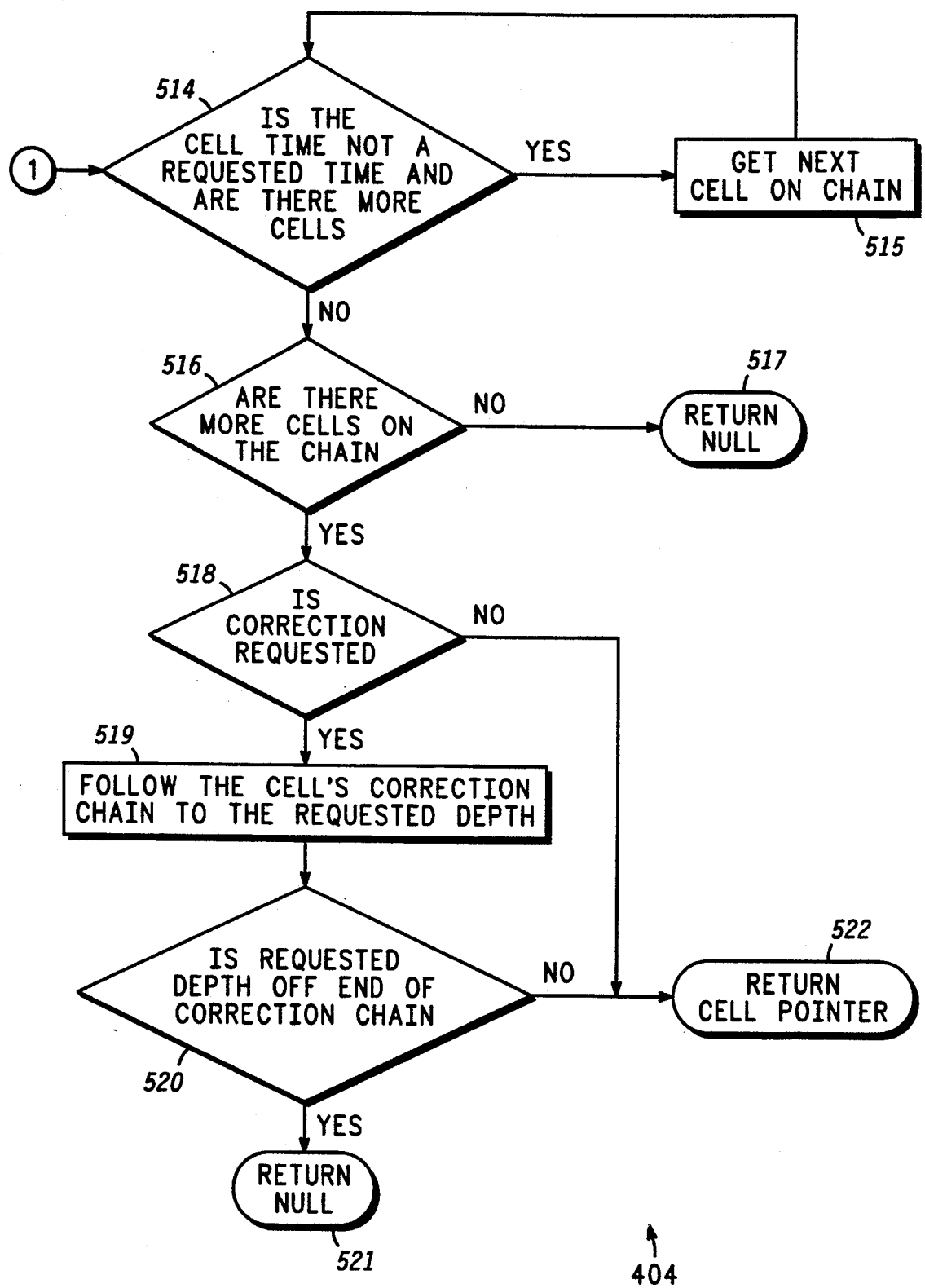

Referring now to FIGS. 13A and 13B, subprocess 404 of FIG. 8 is illustrated in more detail. Pseudo code for subprocess 404 is provided in Appendix E. Subprocess 404 commences at start 504 and moves to decision step 505 where it determines if there are object instances defined for the row descriptor. If there are no object instances defined, the subprocess moves to error step 506. If there are object instances defined, subprocess 404 moves to decision step 507.

In decision step 507, the subprocess determines if the requested time is outside the row descriptor bind. If the requested time is outside the row descriptor bind, the subprocess returns a warning, step 508. If the requested time is not outside the row descriptor bind, the subprocess advances to step 509.

In step 509, subprocess 404 gets the page and column of the requested cell. The subprocess then gets the offset of the row that contains the cell, step 510, and gets the cell offset, step 511.

Following step 511, subprocess 404 moves to decision step 512 and determines if the cell offset is valid. If the cell offset is not valid, the subprocess returns a null, step 513. If the cell offset is valid, subprocess 404 moves to decision step 514, FIG. 13B.

In decision step 514, the subprocess determines if the cell time is not a requested time and if there are more cells. If the conditions of decision step 514 are met, the subprocess gets the next cell on the chain, step 515, and returns to step 514. If the conditions of decision step 514 are not met, the subprocess moves to decision step 516.

In decision step 516, subprocess 404 determines if there are more cells in the chain. If there are no more cells on the chain, the subprocess returns a null, step 517. If there are cells remaining on the chain, the subprocess advances to decision step 518 where the subprocess determines if a correction is requested.

If a correction is requested, the subprocess follows the cell's correction chain to the requested depth, step 519. The subprocess then moves to decision step 520 and determines if the requested depth is off the end of the correction chain. If the requested depth is off the end of the correction chain, the subprocess returns a null, step 21. If the requested depth is not off the end of the chain, step 520, or if the correction is not requested, step 518, the subprocess returns the cell pointer, step 22.

Therefore, a process has been shown which accomplishes the objectives of storing and retrieving data in a faster, more efficient manner. Further, the present invention automatically provides an audit trail for structure types of the object instances.

Thus, it will be apparent to one skilled in the art that there has been provided in accordance with the invention, a data organization scheme that fully satisfies the objects, aims, and advantages set forth above.

While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

APPENDIX A

Define a Set of Objects

Allocate a row descriptor.
Initialize the row descriptor.
For each object specified by the application do
Look up the object description in the object table.
If the object description is not in the object table, there is an error (all objects must be defined in the object table)—don't continue.
Add the table object definition to the row descriptor.

APPENDIX B

Bind a Set of Objects

If there are no objects defined for the row descriptor
This is an error condition—don't continue.
If none of the objects defined for the row descriptor (RD) are indexed-matrix objects
Return zero to the application—No rows bound because only indexed-matrix rows can be bound.
Set the bind times in the RD to the requested start and end bind times.
If the application did not specify the number of columns to bind
If both end points of the bind time range are not defined
This is an error condition—the application must either specify the number of columns to bind, or both end points of the bind time range—don't continue.
Swap the start and end bind times if the requested direction is "older" so that start time is less than end time.
Build the row list for the specified bind time range
Return to the application.
Set the RD start and end times (NOT the bind times) to the start and end times of what is actually in the database between (and including, if possible) the requested start date and the edge of the database going in the requested direction (older or newer).
If the requested direction is "newer"
If the requested start time is before the actual database start time, set the requested start time to the actual database start time.

If the requested start time is past the actual database end time, then there are no columns available for the requested time frame, so return "zero columns bound".

If the requested direction is "older" (reverse chronological order—requested time is end time)

If the requested end time is after the actual database end time, set the requested end time to the actual database end time.

If the requested end time is before the actual database start time, then there are no columns available for the requested time frame, so return "zero columns bound".

Define the bind set boundaries, count the columns in the bind set, and save the times of the columns bound If only one time was specified
If there are columns in the bind set
  Set the bind set end time in the RD to the time of the last column in the bind set.
Else
  Set the bind set end time in the RD to the bind set start time in the RD to indicate that there are no columns in the bind set
If the requested direction is "older"
Swap the start and end bind set times in the RD so that start time is less than end time.
Build the row list for the bound time range
Return the number of columns in the bind set.

APPENDIX C

Build Row List

Free the row descriptor's current row list (if there is one).

Set the row descriptor start and end times to the start and end times of what is actually in the database.

If the bind range of the indexed-matrix rows is outside of the actual database time range, then there are no rows to build—return.

For each indexed-matrix object definition in the row descriptor do
Find the first page in memory whose time range is part of the bind set and get the column number within the page of the time closest to the start time of the bind set.
Try to find the last page of times in the bind set.
Start with the first page whose time range is part of the bind set—while there are more pages whose time ranges are part of the bind set do
  For each row on the page that matches the current object definition do
    Get the address of the row header in the data space using the OCHI index.
    If either the row start time or end time are in the bind set, add the row to the end of the row descriptor's row list.
  Get the next page with times in the bind set (if any remain).

APPENDIX D

Bind Columns

While within the requested time range (if specified) AND the next time to bind (based on highest row density) will not fill all available columns in the bind set AND the next time to bind (based on highest density) is within the database time range do
For each object definition in RD that is indexed-matrix do If the density of the object is more than that of all previous objects, save the density.
Get the page number within the block, and the column number within the page of the time to include in the bind set.
Get the Object Class Hierarchy Index (OCHI) and I-indexes and the data for the page.
Find the first entry in the OCHI index for the object definition.
If the object is not in the OCHI index for this page, then it has no data in the page's time range—move on the next object (go to the top of the for loop).
For each row on the page with the current object definition do
  Get the address of the row in the data space for the page (using the OCHI index).
  Get the offset into the data space of the cell header within the row.
  If the cell header offset is not valid, there is no data on this page on this row for this particular column—do the next row.
If the requested direction is "older"
  Go to the end of the cell chain to prepare to traverse it backwards—note that the cell chain includes cells with times for the current cell up to, but not including, the time for the next regular cell for the density.
While there are more cells in the cell chain and there is room in the bind set for more columns do
  Save the cell time in the bind set.
  Get the next cell (in the proper direction) on the cell chain.

APPENDIX E

Get an Object Instance or Correction Cell

If no objects are defined for the row descriptor
Don't continue—this is an error condition.
If the requested cell time is outside of the RD bind set time range
Return a null value—issue a warning.
Get the page within the block, and the column within the page of the requested cell
From the page's I-index, get the offset into the data space of the row that contains the cell.
Get the cell offset from the row.
If the cell offset is not valid
There is no data for the requested cell, so return a null value.
While the cell time is not the same as the requested time and there are more cells on the chain do
Go to the next cell on the cell chain.
If there are no more cells on the cell chain
There is no data for the requested cell, so return a null value.
If a corrected value was requested
Follow the cell's correction chain to the requested depth.
If the end of the correction chain is reached before the requested depth
There is no correction cell at the requested depth for this time so return a null value.
Return a pointer to the cell found.

We claim:

1. In a computer system having input means for inputting data and commands into said system by a system user, display means for displaying information to said user, a memory for storing data and instructions, including a database, said database comprising a plurality of data cells, and a transaction engine for performing operations upon said database in response to the entry of data and commands into said system by said user using said input means, a computer-implemented process for creating and providing to the user, at the user's option by entering a request therefor, a data audit trail in said system, wherein some or all of the steps in said process are performed by said transaction engine, said process comprising the steps of:

a) said transaction engine creating a primary linked list of a number N of said data cells, said number N being a positive, non-zero integer which is less than said plurality, said primary linked list linking data in a first of said data cells to data in a second of said data cells, said primary linked list linking data in said second data cell to data in a third of said data cells, and so forth, with data in the (N−1)th data cell being linked to data in the Nth data cell in said N data cells;

b) said transaction engine reading an original data of an original data cell of said N data cells from said database;

c) said user modifying the original data read by said transaction engine and thereby forming a modified data;

d) said transaction engine storing said modified data in a data cell in said database as a modified data cell which is not one of said N data cells;

e) said transaction engine linking said modified data cell into said primary linked list and unlinking said original data cell from said primary linked list;

f) said transaction engine creating a secondary linked list, said secondary linked list linking said modified data in said modified data cell to said original data cell;

g) in response to a request to view modified data entered into said system by said user, said transaction engine using said primary linked list to retrieve and display data stored in at least a portion of said N data cells, including said modified data; and h) in response to a request to view original data entered into said system by said user, said transaction engine using said secondary linked list to retrieve and display said original data stored in said original data cell;

whereby, upon request of said user to view said N data cells or a portion thereof, either said modified data or said original data is displayed, depending upon said user's request, thereby permitting said user, at his option, to review either said modified data or an audit trail which includes said original data.

2. In a computer system having input means for inputting data and commands into said system by a system user, display means for displaying information to said user, a memory for storing data and instructions, including a database, said database comprising a plurality of data cells, and a transaction engine for performing operations upon said database in response to the entry of data and commands into said system by said user using said input means, a computer-implemented process for creating and providing to the user, at the user's option by entering a request therefor, a data audit trail in said system, wherein some or all of the steps in said process are performed by said transaction engine, said process comprising the steps of:

a) said transaction engine creating a primary linked list of a number N of said data cells, said number N being a positive, non-zero integer which is less than said plurality, said primary linked list linking data in a first of said data cells to data in a second of said data cells, said primary linked list linking data in said second data cell to data in a third of said data cells, and so forth, with data in the (N−1)th data cell being linked to data in the Nth data cell in said N data cells;

b) said transaction engine reading an original data of an original data cell of said N data cells from said database;

c) said user modifying the original data read by said transaction engine and thereby forming a modified data;

d) said transaction engine storing said modified data in a data cell in said database as a modified data cell which is not one of said N data cells;

e) said transaction engine creating a secondary linked list, said secondary linked list linking said modified data in said modified data cell to said original data cell;

f) in response to a request to view original data entered into said system by said user, said transaction engine using said primary linked list to retrieve and display data stored in at least a portion of said N data cells, including said original data; and g) in response to a request to view modified data entered into said system by said user, said transaction engine using said secondary linked list to retrieve and display said modified data stored in said modified data cell;

whereby, upon request of said user to view said N data cells or a portion thereof, either said original data or said modified data is displayed, depending upon said user's request, thereby permitting said user, at his option, to review either an audit trail which includes said original data or said modified data.

* * * * *